US012611480B2

(12) United States Patent
Tsuji et al.

(10) Patent No.: US 12,611,480 B2
(45) Date of Patent: Apr. 28, 2026

(54) HYDROPHILIC COMPOUND REMOVAL METHOD AND ODOR REMOVAL METHOD

(71) Applicant: DAIKIN INDUSTRIES, LTD., Osaka (JP)

(72) Inventors: Masayuki Tsuji, Osaka (JP); Taku Yamanaka, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 960 days.

(21) Appl. No.: 16/966,941

(22) PCT Filed: Feb. 5, 2019

(86) PCT No.: PCT/JP2019/003935
§ 371 (c)(1),
(2) Date: Aug. 3, 2020

(87) PCT Pub. No.: WO2019/156037
PCT Pub. Date: Aug. 15, 2019

(65) Prior Publication Data
US 2021/0046209 A1 Feb. 18, 2021

(30) Foreign Application Priority Data
Feb. 7, 2018 (JP) ................................. 2018-020456

(51) Int. Cl.
| | |
|---|---|
| *C08F 6/10* | (2006.01) |
| *A61L 9/18* | (2006.01) |
| *C08F 6/00* | (2006.01) |
| *C08F 6/16* | (2006.01) |
| *C08F 6/28* | (2006.01) |
| *C08J 3/28* | (2006.01) |
| *B08B 7/00* | (2006.01) |
| *C08F 114/26* | (2006.01) |

(52) U.S. Cl.
CPC .................. *A61L 9/18* (2013.01); *C08F 6/00* (2013.01); *C08F 6/10* (2013.01); *C08F 6/16* (2013.01); *C08F 6/28* (2013.01); *C08J 3/28* (2013.01); *B08B 7/0035* (2013.01); *C08F 114/26* (2013.01)

(58) Field of Classification Search
CPC ....................................................... A61L 9/18
See application file for complete search history.

(56) References Cited

U.S. PATENT DOCUMENTS

| | | | | | |
|---|---|---|---|---|---|
| 3,721,638 | A | * | 3/1973 | Sianesi ................... | C08F 14/26 526/208 |
| 4,535,136 | A | * | 8/1985 | Wheland ................. | C08F 14/18 526/214 |
| 11,326,034 | B2 | * | 5/2022 | Ikeda ................... | C09D 127/18 |
| 2002/0161067 | A1 | * | 10/2002 | Udagawa ................... | C08J 3/28 525/200 |
| 2003/0229167 | A1 | * | 12/2003 | Baron ........................ | C08J 3/16 524/265 |
| 2004/0072977 | A1 | * | 4/2004 | Kaulbach .............. | C08F 114/18 526/247 |
| 2004/0143052 | A1 | * | 7/2004 | Epsch .................. | C09D 127/12 524/544 |
| 2007/0059445 | A1 | | 3/2007 | Coates et al. | |
| 2007/0117929 | A1 | * | 5/2007 | Burch ................... | C08L 51/003 525/199 |
| 2017/0260344 | A1 | * | 9/2017 | Imamura ............. | C08F 214/262 |

FOREIGN PATENT DOCUMENTS

| | | | |
|---|---|---|---|
| EP | 3 733 742 A1 | | 11/2020 |
| EP | 3 750 947 A1 | | 12/2020 |
| JP | 2002327068 | * | 11/2002 |
| JP | 2005-154277 A | | 6/2005 |
| JP | 2005-523964 A | | 8/2005 |
| JP | 2007-083096 A | | 4/2007 |
| JP | 2007137982 | * | 6/2007 |
| JP | 2013064105 A | | 4/2013 |
| WO | 03/091318 A1 | | 11/2003 |
| WO | WO 2017/043372 | * | 3/2017 |

OTHER PUBLICATIONS

Ma et al, Nucl Sci Tech, 2017, 28:137 (Year: 2017).*
Nichipor et al, Pollution Control Technologies Laboratory, Annual Report, 2016 (Year: 2016).*
JP2002327068 translation (Year: 2002).*
JP2007137982 translation (Year: 2007).*
Extended European Search Report dated Aug. 5, 2021 in Application No. 19751066.2.
Ze Zhang et al., "Complete mineralization of perfluorooctanoic acid (PFOA) by $\gamma$-irradiation in aqueous solution", Scientific Reports, vol. 4, No. 7418, 2014, pp. 1-6 (6 pages total).
"Use of radiation in decomposition and removal of environmentally hazardous compound", Research Organization for Information Science and Technology (RIST), Dec. 4, 2017.
International Search Report for PCT/JP2019/003935 dated May 14, 2019 [PCT/ISA/210].
International Preliminary Report on Patentability with translation of Written Opinion dated Aug. 11, 2020, in Application No. PCT/JP2019/003935.
Lunkwitz et al., "Modification of perfluorinated polymers by high-energy irradiation", Journal of Fluorine Chemistry, vol. 125, 2004, pp. 863-873.

* cited by examiner

*Primary Examiner* — Irina Krylova
(74) *Attorney, Agent, or Firm* — Sughrue Mion, PLLC

(57) ABSTRACT

The disclosure provides a method for removing a C4-C20 hydrophilic compound. The method for removing a hydrophilic compound includes step (a) of exposing a composition containing a C4-C20 hydrophilic compound to 0.1 to 500 kGy of radiation to remove the hydrophilic compound.

2 Claims, No Drawings

HYDROPHILIC COMPOUND REMOVAL METHOD AND ODOR REMOVAL METHOD

CROSS REFERENCE TO RELATED APPLICATIONS

This application is a National Stage of International Application No. PCT/JP2019/003935 filed Feb. 5, 2019, claiming priority based on Japanese Patent Application No. 2018-020456 filed Feb. 7, 2018.

TECHNICAL FIELD

The disclosure relates to methods for removing a hydrophilic compound and deodorization methods.

BACKGROUND ART

Use of radiation has been proposed for decomposition and removal of harmful substances and environmentally hazardous compounds, such as organochlorine hydrocarbons or heavy-metal ions (see Non-Patent Literature 1).

CITATION LIST

Non-Patent Literature

Non-Patent Literature 1: Research organization for Information Science & Technology (RIST) (July 2006), "Kankyou-fuka kagoubutu no bunkai/jokyo ni okeru houshasen riyou [Use of radiation for decomposition/removal of environmentally hazardous compounds]", accessed Dec. 4, 2017, from URL: http://www.rist.or.jp/atomica/data/dat_detail.php?Title_Key=08-03-03-04

SUMMARY OF INVENTION

Technical Problem

The disclosure aims to provide a method for removing a C4-C20 hydrophilic compound or an odor.

Solution to Problem

The disclosure relates to a method for removing a hydrophilic compound including step (a) of exposing a composition containing a C4-C20 hydrophilic compound to 0.1 to 500 kGy of radiation to remove the hydrophilic compound from the composition.

The hydrophilic compound includes preferably at least one selected from the group consisting of C4-C20 fluorine-containing carboxylic acids and salts thereof and C4-C20 fluorine-containing sulfonic acids and salts thereof.

The composition preferably contains a polymer.

The polymer is preferably a fluorine-containing polymer.

The disclosure also relates to a deodorization method including step (b) of exposing an object filling an airtight container to 0.1 to 500 kGy of radiation from outside of the airtight container to reduce an odor intensity of the object to 2 or less.

The object preferably contains a polymer.

The polymer is preferably a fluorine-containing polymer.

Advantageous Effects of Invention

The disclosure can provide a method for removing a C4-C20 hydrophilic compound or an odor.

DESCRIPTION OF EMBODIMENTS

The disclosure is specifically described in the following.

The disclosure relates to a method for removing a hydrophilic compound including step (a) of exposing a composition containing a C4-C20 hydrophilic compound to 0.1 to 500 kGy of radiation to remove the hydrophilic compound from the composition (hereafter, also referred to as a first method).

In the first method, exposure to a specific dose of radiation enables removal of the hydrophilic compound from the composition.

The radiation in the step (a) is not limited as long as it is an ionizing radiation, and examples thereof include electron beams, UV rays, gamma rays, X rays, neutron beams, and high-energy ions. Preferred are electron beams and gamma rays.

The exposure dose in the step (a) is 0.1 to 500 kGy. The exposure dose is preferably 250 kGy or less, more preferably 200 kGy or less. In cases where the object contains polytetrafluoroethylene (PTFE), the exposure dose is still more preferably 15 kGy or less. The exposure dose is preferably 0.5 kGy or more, more preferably 1.0 kGy or more.

The exposure temperature in the step (a) is preferably 5° C. to 320° C., more preferably 300° C. or lower, still more preferably 260° C. or lower. From an economic point of view, the exposure is preferably performed at room temperature.

The exposure to radiation in the step (a) may be carried out in any atmosphere. For example, the exposure can be carried out in the air, in an inert gas, or in a vacuum. The exposure in the air is preferred as it can be carried out at a low cost.

The hydrophilic compound has a carbon number of 4 to 20. The hydrophilic compound having a carbon number within the above range contains non-naturally occurring, difficult-to-decompose or highly bioaccumulative substances, and therefore is preferably removed. The carbon number is preferably 6 or higher, more preferably 8 or higher. The carbon number is preferably 14 or lower.

The hydrophilic compound is a compound having a hydrophilic group. Examples of the hydrophilic group include a carboxyl group (—COOH) and its salt type group, and a sulfo group (—SO₃H) and its salt type group. In particular, the hydrophilic group is preferably at least one selected from the group consisting of a carboxyl group (—COOH) and its salt type group and a sulfo group (—SO₃H) and its salt type group, more preferably at least one selected from the group consisting of a carboxyl group (—COOH) and its salt type group.

The hydrophilic compound has preferably a halogen atom, more preferably a fluorine atom.

Examples of the hydrophilic compound include C4-C20 fluorine-containing carboxylic acids and salts thereof, and C4-C20 fluorine-containing sulfonic acids and salts thereof. These all may have an ether bond (—O—).

In particular, the hydrophilic compound is preferably at least one selected from the group consisting of C4-C20 fluorine-containing carboxylic acids and salts thereof and C4-C20 fluorine-containing sulfonic acids and salts thereof, more preferably at least one selected from the group consisting of C4-C20 perfluorocarboxylic acids and salts thereof and C4-C20 perfluorosulfonic acids and salts thereof, still more preferably at least one selected from the group consisting of C4-C20 perfluorocarboxylic acids and salts thereof.

The hydrophilic compound content of the composition to be exposed to radiation in the step (a) is preferably more than 50 ppb on a mass basis. The upper limit is not limited, and may be, for example, 1% by mass.

The composition preferably further contains a polymer. Examples of the polymer include fluorine-free polymers and fluorine-containing polymers. Preferred are fluorine-containing polymers.

Examples of the fluorine-free polymers include polycarbonate, polyamide, POM, PPS, polyethylene, and polypropylene.

Examples of the fluorine-containing polymers include a fluororesin and a fluoroelastomer. Preferred is a fluororesin.

The fluororesin has a melting point of preferably 100° C. to 360° C., more preferably 140° C. to 350° C., still more preferably 160° C. to 350° C., particularly preferably 180° C. to 350° C.

The melting point of the fluororesin is a temperature corresponding to the maximum value in the melting heat curve obtained by increasing a temperature at a rate of 10° C./min using a differential scanning calorimeter (DSC).

Examples of the fluororesin include polytetrafluoroethylene [PTFE], tetrafluoroethylene [TFE]/perfluoro(alkyl vinyl ether) [PAVE] copolymers [PEA], TFE/hexafluoropropylene [HFP] copolymers [FEP], ethylene [Et]/TFE copolymers [ETFE], TFE/vinylidene fluoride [VDF] copolymers, Et/TFE/HFP copolymers, polychlorotrifluoroethylene [PCTFE], chlorotrifluoroethylene [CTFE]/TFE copolymers, VDF/CTFE copolymers, Et/CTFE copolymers, polyvinylidene fluoride [PVDF], and polyvinyl fluoride [PVF]. Preferred among these is PTFE.

The PTFE may be homogeneous PTFE consisting only of TFE units or modified PTFE including a TFE unit and a modifying monomer unit based on a modifying monomer copolymerizable with TFE.

In the modified PTFE, the modifying monomer unit content is preferably 0.0001 to 0.5% by mass, more preferably 0.001% by mass or more, still more preferably 0.01% by mass or more of all the monomer units. The modifying monomer unit content is more preferably 0.3% by mass or less, still more preferably 0.2% by mass or less. Herein, the modifying monomer unit refers to a part that is a portion of the molecular structure of the modified PTFE and is derived from a modifying monomer. The term "all the monomer units" refers to all the parts derived from monomers in the molecular structure of the modified PTFE. The modifying monomer unit content can be obtained by a known method such as Fourier transform infrared spectroscopy (FT-IR).

Examples of the modifying monomer include perhaloolefins such as HFP and CTFE; fluoro (alkyl vinyl ethers) having a C1-C5, particularly C1-C3 alkyl group; cyclic fluorinated monomers such as fluorodioxole; perhaloalkyl ethylenes; and ω-hydroperhaloolefins.

The PTFE may be high-molecular-weight PTFE or low-molecular-weight PTFE.

The high-molecular-weight PTFE has a standard specific gravity (SSG) of 2.130 to 2.230. The standard specific gravity (SSG) is a value determined in conformity with ASTM D 4895. The "high molecular weight" as used herein means that the standard specific gravity is within the above range.

The low-molecular-weight PTFE has a melt viscosity at 380° C. of $1.0 \times 10^2$ to $7.0 \times 10^5$ Pa·s. The melt viscosity is preferably $1.5 \times 10^3$ Pa·s or higher but is preferably $3.0 \times 10^5$ Pa·s or lower, more preferably $1.0 \times 10^5$ Pa·s or lower.

The melt viscosity is a value determined by heating a 2-g sample at 380° C. for five minutes in advance and then keeping this sample at this temperature under a load of 0.7 Mpa using a flow tester (produced by Shimadzu Corporation) and a 2$\phi$-8 L die in conformity with ASTM D 1238.

The "low molecular weight" as used herein means that the melt viscosity is within the above range.

The polymer content relative to the composition is preferably 0% by mass or more but less than 100% by mass. The polymer content may be 0.01% by mass or more.

The composition may further contain water or an organic solvent. The composition preferably contains water.

The water- or organic solvent content relative to the composition is preferably 0% by mass or more but less than 100% by mass. The water- or organic solvent content may be 0.01% by mass or more.

The composition may be, for example, a powder, pellet, solution, or dispersion containing the polymer. The solution and the dispersion may be those obtained by polymerization of the polymer.

The composition may be a waste liquid resulting from the isolation of the polymer from the solution or the dispersion.

In the first method, a composition substantially free from C4-C20 hydrophilic compounds can be obtained after the step (a). The composition obtained by the first method contains the hydrophilic compound in a total amount of preferably 50 ppb or less, more preferably less than 25 ppb, still more preferably 15 ppb or less, particularly preferably 5 ppb or less, most preferably less than 5 ppb on a mass basis. The lower limit is not limited, and may be less than the detection limit.

The amount of the hydrophilic compound can be measured by liquid chromatography.

The composition obtained by the first method is also characterized in that it is substantially free from C4-C20 perfluorocarboxylic acids and salts thereof. The total amount of the C4-C20 perfluorocarboxylic acid and salts thereof is preferably 50 ppb or less, more preferably less than 25 ppb, still more preferably 15 ppb or less, particularly preferably 5 ppb or less, most preferably less than 5 ppb, on a mass basis. The lower limit is not limited, and may be less than the detection limit.

The amounts of the perfluorocarboxylic acid and salts thereof can be measured by liquid chromatography.

The composition obtained by the first method is also characterized in that it is substantially free from perfluorooctanoic acid and salts thereof. The composition obtained by the first method contains the perfluorooctanoic acid and salts thereof in an amount of less than 25 ppb on a mass basis, more preferably 15 ppb or less, still more preferably 5 ppb or less, particularly preferably less than 5 ppb. The lower limit is not limited, and the amount may be less than the detection limit.

The amounts of the perfluorooctanoic acid and salts thereof can be measured by liquid chromatography.

The composition obtained by the first method is also characterized in that it is substantially free from C4-C20 perfluorosulfonic acid and salts thereof. The composition obtained by the first method contains the C4-C20 perfluorosulfonic acid and salts thereof in an amount of preferably less than 25 ppb on a mass basis. The amount is more preferably 15 ppb or less, still more preferably 5 ppb or less, particularly preferably less than 5 ppb. The lower limit is not limited, and the amount may be less than the detection limit.

The amounts of the perfluorosulfonic acid and salts thereof can be measured by liquid chromatography.

The disclosure also relates to a deodorization method including step (b) of exposing an object filling an airtight container to 0.1 to 500 kGy of radiation from outside of the airtight container to reduce an odor intensity of the object to 2 or less (hereafter, also referred to as a second method).

In the second method, exposure to a specific dose of radiation enables removal (reduction) of an odor of an object.

The radiation in the step (b) is not limited as long as it is an ionizing radiation, and examples thereof include electron beams, UV rays, gamma rays, X rays, neutron beams, and high-energy ions. Preferred are electron beams or gamma rays.

The exposure dose in the step (b) is 0.1 to 500 kGy. The exposure dose is preferably 200 kGy or less. In cases where the object contains PTFE, the exposure dose is more preferably 15 kGy or less. The exposure dose is preferably 0.5 kGy or more, more preferably 1.0 kGy or more.

The exposure temperature in the step (b) is preferably 5° C. to 320° C., more preferably 300° C. or lower, still more preferably 260° C. or lower. From an economic point of view, the exposure is preferably performed at room temperature.

The exposure to radiation in the step (b) may be carried out in any atmosphere. The exposure can be carried out, for example, in the air, in an inert gas, or in a vacuum according to the atmosphere inside the airtight container.

The airtight container refers to a container which can be sealed up. The airtight container may be coupled with a pipe for intake and exhaust of a gas, and may be coupled with components such as pipes, caps, valves, and flanges which are closed during the exposure to radiation. The airtight container may have any shape, such as a cylindrical shape, a prismatic shape, or a spherical shape, or may be a bag with a variable capacity. The airtight container may be formed of any material, such as metal, glass, or a polymer. The material and structure of the airtight container need to be radiolucent and not deteriorated by exposure to radiation. The airtight container needs not to be a pressure-resistant container.

The object exposed to radiation in the step (b) may have an odor intensity of more than 2. The upper limit of the odor intensity is not limited, but is 6.

The odor intensity is measured in-house in conformity with "Calculation Method of Odor Index and Odor Intensity" (Environment Agency Notification No. 63), the guideline introduced by Ministry of the Environment, and determined based on "six grade odor intensity measurement method".

The object contains an odor substance. The odor substance is not limited, and examples thereof include fluorine-containing compounds. Specific examples thereof include hydrogen fluoride (hydrofluoric acid) and perfluoropropionic acid.

The object preferably contains a polymer.

Examples of the polymer include the polymers exemplified in the description of the first method. Preferred are fluorine-containing polymers, and more preferred is PTFE.

The polymer content relative to the object is preferably 0% by mass or more but less than 100% by mass. The polymer content may be 0.01% by mass or more.

In the step (b), the exposure to radiation reduces the odor intensity of the object to 2 or less. The detail of this mechanism is not clear. Presumably, the odor substance contained in the object is decomposed by the exposure to radiation.

The odor intensity after the exposure is preferably 1 or less. The lower limit of the odor intensity is not limited, and may be 0.

The second method is suitably used, for example, for removing the odor of the polymers or the like filling drum containers or bags.

EXAMPLES

The disclosure is more specifically described with reference to, but not limited to, examples.

The parameters in examples were measured by the following methods.

Amount of Perfluorooctanoic Acid and Salts Thereof (PFOA)

The amount of perfluorooctanoic acid and salts thereof was measured with a liquid chromatography-mass spectrometer (LC-MS ACQUITY UPLC/TQD, Waters). Measurement sample (1 g) was mixed with acetonitrile (5 ml) and the mixture was sonicated for 60 minutes, so that perfluorooctanoic acid was extracted. The resulting liquid phase was analyzed by multiple reaction monitoring (MRM). Acetonitrile (A) and an aqueous ammonium acetate solution (20 mmol/L) (B) were passed at a predetermined concentration gradient (A/B=40/60 for two minutes and 80/20 for one minute) as mobile phases. A separation column (ACQUITY UPLC BEH C18 1.7 μm) was used at a column temperature of 40° C. and an injection volume of 5 μL. Electrospray ionization (ESI) in a negative mode was used as the ionization method, and the cone voltage was set to 25 V. The ratio of the molecular weight of precursor ions to the molecular weight of product ions was measured to be 413/369. The amount of perfluorooctanoic acid and salts thereof was calculated by the external standard method. The detection limit of this measurement is 5 ppb.

Odor Intensity

The odor intensity was measured in-house in conformity with "Calculation Method of Odor Index and Odor Intensity" (Environment Agency Notification No. 63), the guideline introduced by Ministry of the Environment, and determined based on "six grade odor intensity measurement method".

Comparative Example 1

A PTFE fine powder containing 1 ppm of PFOA was used.

Example 1

A PTFE fine powder containing 1 ppm of PFOA was exposed to 10 kGy of cobalt-60γ rays. Then, the PFOA content was measured. Table 1 shows the result.

Example 2

An aqueous solution containing 50 ppm of PFOA was exposed to 100 kGy of cobalt-60γ rays. Then, the PFOA content was measured. Table 1 shows the result.

Example 3

An aqueous solution containing 100 ppm of PFOA was exposed to 250 kGy of cobalt-60γ rays. Then, the PFOA content was measured. Table 1 shows the results.

Example 4

An aqueous solution containing 1% by mass of PFOA was exposed to 500 kGy of cobalt-60γ rays. Then, the PFOA content was measured. Table 1 shows the result.

Comparative Example 2

The odor intensity of a PTFE molding powder sealed in a plastic bag for 100 days was measured. Table 1 shows the result.

Example 5

A PTFE molding powder sealed in a plastic bag for 100 days was exposed to 5 kGy of cobalt-60γ rays. Then, the odor intensity was measured. Table 1 shows the result.

TABLE 1

| | Object substance | Cobalt-60 γ rays Exposure dose | PFOA content | Odor intensity |
|---|---|---|---|---|
| Comparative Example 1 | PTFE fine powder containing 1 ppm of PFOA | 0 | 1 ppm | |
| Example 1 | PTFE fine powder containing 1 ppm of PFOA | 10 kGy | Less than limit of detection | |
| Example 2 | Aqueous solution containing 50 ppm of PFOA | 100 kGy | Less than limit of detection | |

TABLE 1-continued

| | Object substance | Cobalt-60 γ rays Exposure dose | PFOA content | Odor intensity |
|---|---|---|---|---|
| Example 3 | Aqueous solution containing 100 ppm of PFOA | 250 kGy | Less than limit of detection | |
| Example 4 | Aqueous solution containing 1% by mass of PFOA | 500 kGy | Less than limit of detection | |
| Comparative Example 2 | PTFE molding powder sealed in plastic bag for 100 days | 0 | | 5 |
| Example 5 | PTFE molding powder sealed in plastic bag for 100 days | 5 kGy | | 1 |

The invention claimed is:

1. A method for removing a hydrophilic compound comprising:

step (a) of exposing a composition containing perfluorooctanoic acid and salts thereof (PFOA) to 1.0 to 15 kGy of radiation in the air at room temperature, thereby removing the PFOA from the composition, wherein the composition is a polytetrafluoroethylene (PTFE) powder or pellet containing the PFOA, the PFOA content of the composition before exposure to said radiation in the step (a) is more than 1 ppm to 1% by mass, and the PFOA content of the composition after exposure to said radiation in the step (a) is less than 25 ppb by mass.

2. The method according to claim 1, wherein the PTFE in the PTFE powder is PTFE consisting of tetrafluoroethylene units only or the PTFE including a tetrafluoroethylene unit and 0.0001 to 0.5% by mass of a modifying monomer unit based on mass of all the monomer units.

\* \* \* \* \*